United States Patent [19]
Kilcullen

[11] Patent Number: 5,456,704
[45] Date of Patent: Oct. 10, 1995

[54] METHOD OF TREATMENT WITH THERAPEUTIC MOIST HEATING PAD

[76] Inventor: Robert J. Kilcullen, 133 Longdean Rd., Fairfield, Conn. 06430

[21] Appl. No.: 391,827

[22] Filed: Feb. 21, 1995

Related U.S. Application Data

[63] Continuation of Ser. No. 230,665, Apr. 21, 1994, abandoned.

[51] Int. Cl.$^6$ ............................................. A61F 7/00
[52] U.S. Cl. ........................... 607/111; 607/112; 607/114; 383/901
[58] Field of Search ................ 607/108–112, 114; 383/901; 165/46; 62/4, 530; 206/219

[56] References Cited

U.S. PATENT DOCUMENTS

| | | | |
|---|---|---|---|
| 3,804,077 | 4/1974 | Williams | 607/114 |
| 3,889,684 | 6/1975 | Lebold | 607/111 |
| 4,397,315 | 8/1983 | Patel | 607/114 |
| 5,275,156 | 1/1994 | Milligan et al. | 607/114 |
| 5,277,180 | 1/1994 | Angelillo et al. | 607/114 |

Primary Examiner—Lee S. Cohen
Assistant Examiner—Robert L. Nasser, Jr.
Attorney, Agent, or Firm—Norman Friedland

[57] ABSTRACT

A method of applying therapeutic heat a patient including forming a heating pad having an outer container having a first side formed by a material non-pervious to water and a second side formed by a material pervious to water. The container substantially encapsulates an outer bag containing and exothermic chemical and an inner bag containing a solvent. Further, the first side is covered by a layer of heat insulating materially and the second side by a layer of sponge-like material. The fist side and sponge-like material are contacted with water, thereby causing the sponge-like material to absorb water. Then the inner bag is fractured, causing the chemical and solvent to mix, producing heat, which is directed at the sponge-like material. The second side of the heating pad is then placed against the body, causing moist heat to be applied to the body. The pad may by tied to the body using straps extending from the ends of the container.

4 Claims, 4 Drawing Sheets

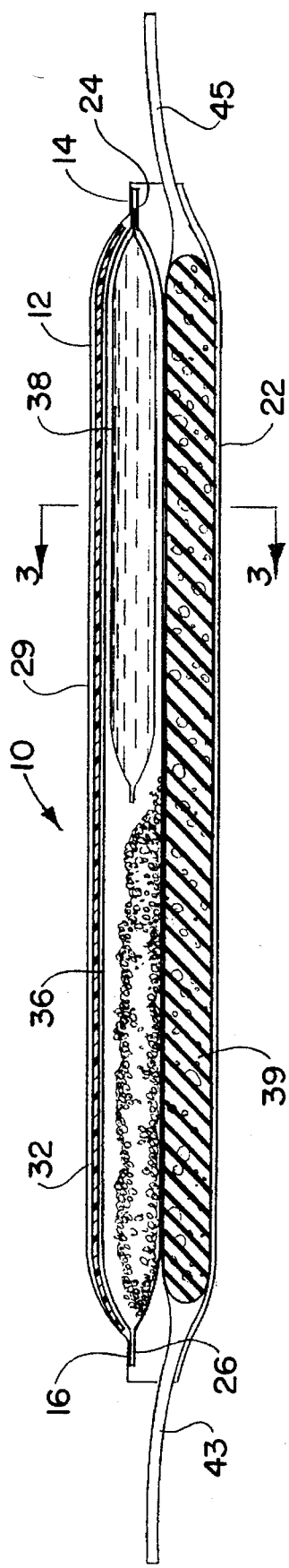
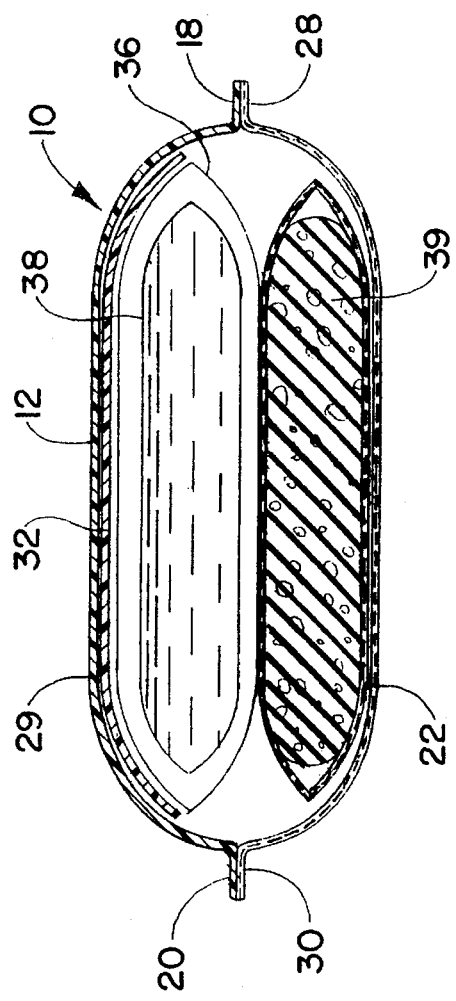
FIG. 2
FIG. 3

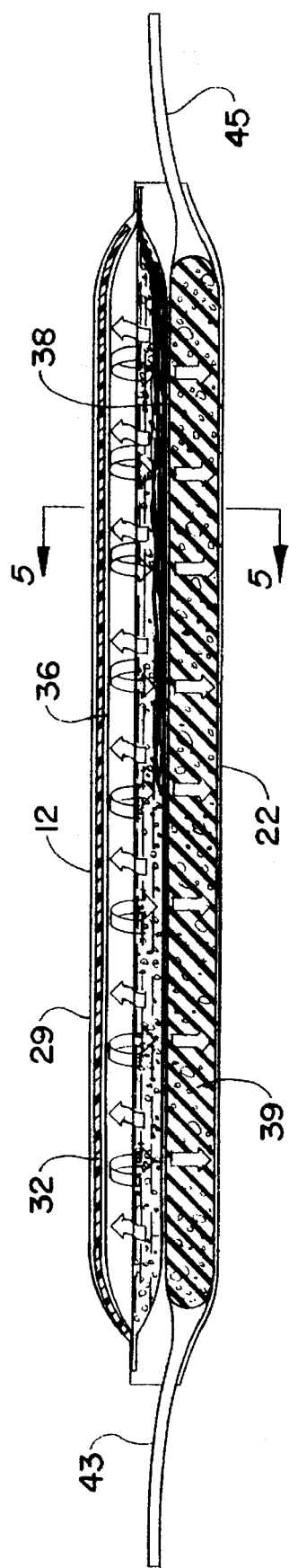
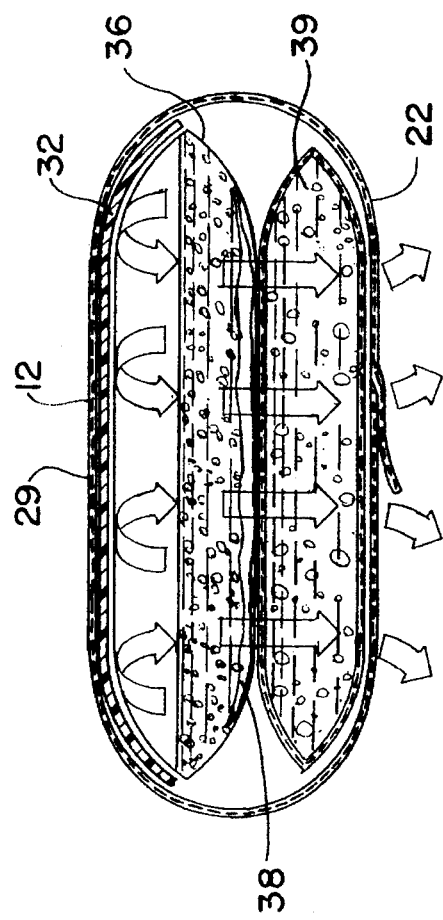
FIG. 4
FIG. 5

5,456,704

METHOD OF TREATMENT WITH THERAPEUTIC MOIST HEATING PAD

This application is a Continuation of U.S. patent application Ser. No. 08/230,665, filed Apr. 21, 1994, now abandoned.

TECHNICAL FIELD

This invention relates to moist heating pads and particularly to a disposable heating moist pad that includes an exothermic solute that mixes with a solvent in order to cause a chemical reaction to generate or liberate heat and includes a water absorbent material in contiguous relationship therewith. The invention includes the disposable moist heating pad adapted to be used in the method of dilating the network of capillary tubes in the heel of an infant for facilitating the process of drawing blood from the infant.

BACKGROUND ART

The use of moist heating pads for therapeutic and dilating purposes have been written up in the literature. For example, U.S. Pat. No. 3,587,578 granted to Walker on Jun. 28, 1971 discloses a heat pack of laterally spaced cells that are fabricated with an inner layer of water pervious material and an outer layer of water impervious material which is molded to form spaced troughs. The material of the outer layer is a stretchable material and the inner layer is a non-stretchable material so as to be configured into a small diameter pack. This construction allows a larger area contact of the anatomy when compared with, for example, the construction of the heat pack described in the Jensen U.S. Pat. No. 2,710,008. The Jensen patent describes a heat pack that is fabricated from a two-sided tightly woven fabric stitched to form laterally spaced cells filled with a bentonite filler. Bentonite is characterized as an amorphous material that is capable of absorbing large volumes of water. Typically, these packs are dipped into hot water for a period of time to be allowed to heat up to the temperature of the boiling water, then removed and wrapped in a Turkish towel and ultimately applied to the desired anatomy of the patient being treated.

U.S. Pat. No. 5,178,139 granted to Angelillo et al on Jan. 12, 1993 discloses a heat pack and absorbent pad combination utilized for obstetrics and gynecology purposes that includes a chemical encased in a plastic bag internal of the pad that undergoes an exothermic reaction when mixed with a solvent to produce heat. An insulating pad is interposed between the plastic bag containing the chemical and the skin of the patient to provide a moderate thermal barrier between the two surfaces.

The pads disclosed in U.S. Pat. Nos. 3,587,578 and 2,710,008, supra, are reusable types and as discussed above require the heating by being immersed into hot water. The pad disclosed in U.S. Pat. No. 5,178,139, supra, is an absorbent pad and is not a heating pad in the same sense as the others inasmuch as the heat is thwarted so that only a minimal heat is allowed to flow toward the anatomy. One of the undesirable characteristics of the heating pads disclosed hereinabove is that it is necessary to preheat the pad by immersing it in hot water. This has a tendency of being initially hot and cooling down very quickly so that the heat varies over time during the course of application. Another disadvantage in the cellular construction is that the area where the adjacent cells are joined has a tendency of being cooler than the area directly under the cell.

My invention obviates the problems alluded to in the above by forming the disposable moist heating pad into a single package consisting of layers of material and including separate packages of the chemicals and solvent. The package includes a water absorbent material adjacent to the bottom layer that defines a continuous flat inner flexible surface that when applied is in contiguous contact with the skin of the patient being treated. The moist heating pad of this invention is disposable and utilizes a sealed chemical and solvent that produces an exothermic reaction when the frangible barrier separating the chemical from the solvent is broken. The face that is applied to the anatomy is formed from a non-woven fabric that is pervious to water and water vapor and allows the adjacent layer of a sponge-like material to absorb water. The volume of water contained in the sponge-like material is heated by the exothermic reaction upon the breaking of the barrier so as to apply a substantially uniform moist heat to the skin of the patient.

This invention is particularly efficacious for use in the medical procedure for obtaining a blood sample from an infant, particularly a premature baby. Typically such procedure includes obtaining the blood samples from the heel by the use of a well known lancet. As is well known, because of the minute diameters of the capillaries in this area of the anatomy, it is difficult or impossible to obtain samples of blood. The heel is preheated and this is typically done by a heated absorbent pad that is previously soaked in hot water. The absorbent pad is removed from the immersed hot water, either wrapped in a towel or the like or aloud to cool to a temperate temperature and then applied to the heel before the incision is made. The heat serves to dilate the capillary tubes and tends to bring them closer to the epidermis layer of the skin of the heel.

This heretofore known procedure in not only inefficient, it is also expensive. Typically, the absorbent material is designed for other procedures where the process of absorbing is the primary objective and the process of immersing the absorbent in hot water is time consuming, requires special attention so that the absorbent material is not applied when it is too hot to avoid scalding, and the heat dissipates relatively rapidly.

The disposable moist heating pad of this invention is ideally suited for this procedure inasmuch as it is less expensive than the absorbent pads that are typically used as was described in the immediately preceding paragraph, is less hostile to the patient, and distributes the heat more uniformly and longer with respect to time.

SUMMARY OF THE INVENTION

An object of this invention is to provide an improved disposable moist heating pad.

A feature of this invention is to provide a disposable moist heating pad for therapeutic use that includes an outer enclosed bag having a water pervious bottom layer of material, a non-pervious top layer of material, an inner bag having a pair of compartments of a solvent and a chemical separated by a frangible wall disposed inside the outer bag, a layer of sponge material between the inner bag and the bottom layer of material and a layer of an insulating water impermeable material disposed between the inner bag and the top layer of material. The chemical when combined with the solvent produces an exothermic reaction.

Another feature of this invention is an improved method of extracting a sample of blood from an infant,s heel including the step of providing an improved disposable moist heating pad with an inner bag formed from impervious material having a pari of compartments containing a solvent and a chemical separated by a frangible wall, an outer bag having an impervious top layer and a water pervious bottom layer, a sponge material between the inner bag and the bottom layer and an insulating material impervious to water disposed between the inner bag and the top layer, soaking said outer bag in water to allow the sponge to fill with water, breaking the frangible wall and attaching the disposable moist heating pad to the heel of the infant over a period of time for dilating the capillary tubes therein and withdrawing a sample of blood therefrom.

The foregoing and other features of the present invention will become more apparent from the following description and accompanying drawings.

BRIEF DESCRIPTION OF DRAWINGS

FIG. 2 is a sectional view taken along the longitudinal axis of the disposable moist heating pad of FIG. 1;

FIG. 3 is a sectional view taken along lines 3—3 of FIG. 1;

FIG. 4 is a sectional view identical with the disposable moist heating pad depicted in FIG. 2 with the heating pad activated;

FIG. 5 is a sectional view taken along lines 5—5 of FIG. 4; and

BEST MODE FOR CARRYING OUT THE INVENTION

Figure 1:
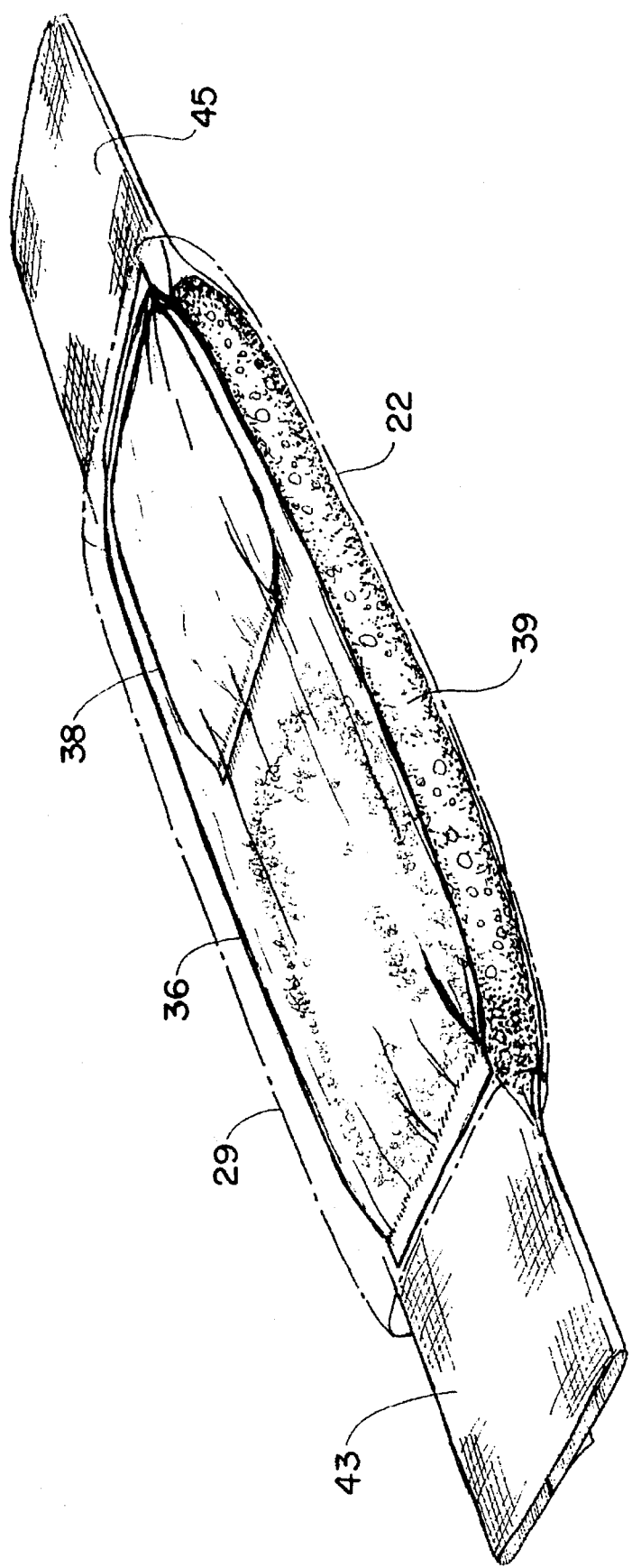
FIG. 1 is a perspective view of the disposable moist heating pad of this invention.

The preferred embodiment of this invention is being described for use as a disposable moist heating pad for both therapeutic purposes and for dilating the blood corpuscles of an infant for obtaining a blood sample from the heel but it is to be understood that the invention is not necessarily limited thereto.

The disposable moist heating pad of this invention generally indicated by reference numeral 10 is best shown in FIGS. 1–5 as having an outer backing sheet 12 that has a generally elongated dimension extending between a first end 14 and a second end 16 and a transverse dimension extending from a first side 18 and a second side 20. The outer backing sheet 12 is preferably made from a flexible liquid impermeable polyethylene material. The front sheet 22 that is placed on the skin of the user is dimensioned to substantially the same dimensions as the backing sheet 12 and likewise has a generally longitudinal dimension extending between a first end 24 and a second end 26 and a generally transverse dimension extending between a first side 28 and a second side 30. The front sheet 22 is preferably fabricated from a suitable liquid permeable non-woven or matted fabric made from a blend (50/50 or 60/40) polypropelene and rayon and is say, 1 to 1.5 ounces per square yards.

The edges of the first ends 14 and 24 and the second ends 16 and 26 and the first sides 18 and 20 and the second sides 28 and 30 are suitably bonded together preferably by a heat sealing method or glued to form an enclosed four sided outer container or bag 29. Preferably, the back cover or backing sheet 12 is say, three (3) millimeter (mil) white polyethylene that prevents liquid from entering or escaping through that surface. The outer or exposed surface of the white polyehtelene material is suitable to be printed on to include indicia, such as instructions for use and a logo, if desired. Alternatively the entire bag may be made from a non-woven fabric similar to the front sheet 22 that wraps around and overlies itself and is sealed in place when fully assembled.

The next layer adjacent the inner face of the back cover 12 is a sheet 32 of insulating material preferably made from closed cell polyethylene and is say, 0.06 inch thick and has a generally longitudinal dimension that is slightly smaller than the longitudinal dimension of the back cover 12 and a generally transverse dimension that is slightly smaller than the transverse dimension of back cover 12. This assures that the generally rectangular or squared shaped insulating material extends just short of the joining edges of the front and backing sheets 22 and 12 although is lies contiguous thereto.

The next layer is a combination inner and outer sealed plastic bags 36 and 38. Sealed bag 36 is dimensioned in the longitudinal and transverse direction substantially identical to the outer bag and the longitudinal dimension of bag 38 is substantially half the length of bag 36. Bag 36 contains the chemical, say sodium acetate or sodium thiosulfate, that when combined with the solute contained in bag 38 produces a chemical exothermic reaction for producing heat. Both bags 36 and 38 are preferably made from polyethylene material and are substantially a mil thick and obviously sealed on all sides. The solute in bag 38 is water that is super saturated with the chemical to obtain the maximum heat output in a controlled manner, i.e. the heat is produced at a substantially constant rate with respect to time.

The last layer 39 is fabricated from a suitable water absorbent material that is deminsioned longitudinally and transversely substantially equal to the same dimensions as the bottom or front sheet 22. Preferably this is a ⅛ inch thick expanded open cell polyethylene material although polyvinyl or other water absorbent material can be used. Like the insulating layer 32, the sponge layer 39 is not attached to the other layers and lies freely in the outer bag 29. When assembled the entire assembly is flexible and can be contoured to fit almost any portion of the anatomy. The sponge layer 39 may be inserted in a wrapped sheet 41 defining a bag formed from a pervious non-woven light weighted fabric that includes elongated ends or tabs 43 and 45 on opposite sides that extend outwardly at the side edges to form a tie that when the disposable moist heat pad is applied the ends or tabs are wrapped around and may overlap to be tied together.

The procedure for applying the disposable moist heat pad to the patient is by first immersing the pad in water to allow the water absorbing material to absorb the water to its maximum capacity. The chemical bag within the disposable moist heating pad is broken by applying pressure to allow the chemical and solute to mix and give off heat. The disposable moist heat pad is then applied to the anatomy of the patient with the outer backing sheet 12 being furthest from the skin. This assures that the water absorbent material is adjacent to the skin and the heat is directed in that direction. Breaking the inner chemical bag affords a dual function. Besides generating heat as described, by squeezing the bag after the sponge is allowed to absorbed the water, the squeezing action expels excessive water that may have been absorbed by the water absorbing material. This eliminates the propensity of the disposable moist heating pad from dripping excessive water and avoids a messy situation.

Figure 6:
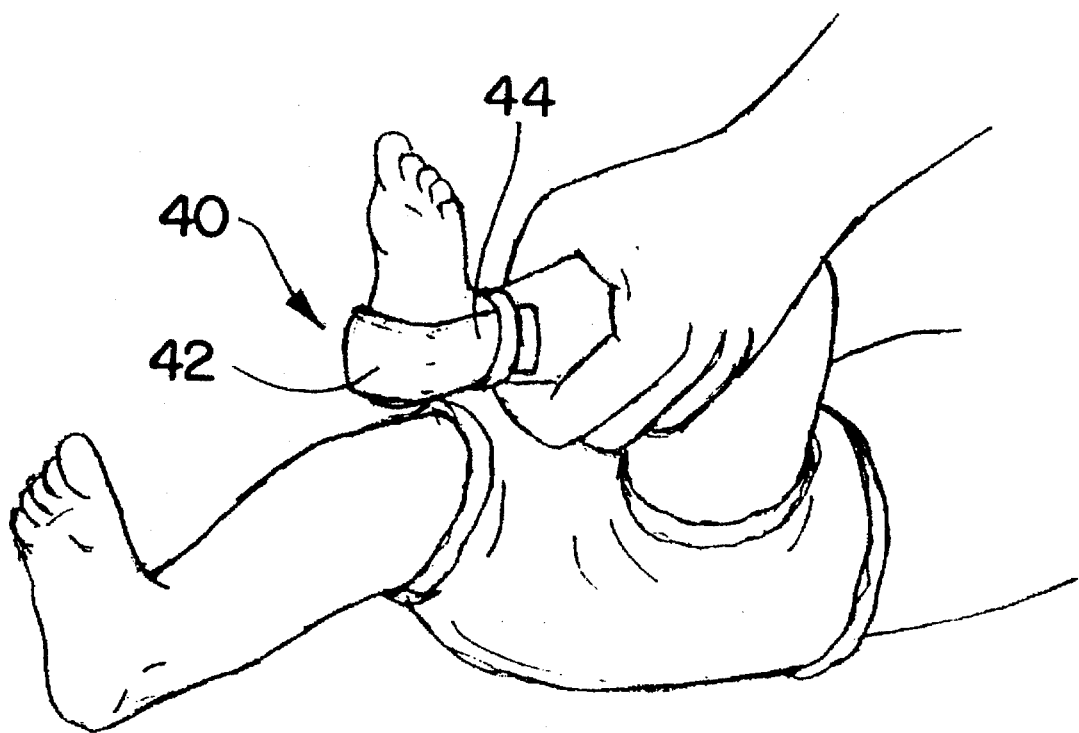
FIG. 6 is a perspective view exemplifying another disposable moist heating pad being applied to the heel of an infant for preparation of extracting a blood sample.

The moist heat pack exemplified in FIG. 6 and generally illustrated by reference numeral 40 is an identically constructed disposable moist heat pad as that depicted in FIGS.

1–5 but is smaller in size to fit the heal of the infant patient. The front sheet 42 which is made from the same material as the front sheet 22 of the prior described moist heat pack includes additional material 44 and 46 extending in the longitudinal direction on either ends of the outer bag for defining tabs to either serve as a tie to the ankle of the infant or to be used as tangs so that a bandage or tape can secure it to the heel. After the pack is immersed in water so that the sponge absorbs the water and the inner plastic bag of solute is ruptured the pack is applied to the patient for a period of time. The pack is then removed and the skin is lanced so as to remove a sample of blood.

Although this invention has been shown and described with respect to detailed embodiments thereof, it will be appreciated and understood by those skilled in the art that various changes in form and detail thereof may be made without departing from the spirit and scope of the claimed invention.

It is claimed:

1. A method of therapeutically heating a portion of an area of a body by applying moist heat comprising the steps of providing a moist heating pad having a flexible inner bag formed from a non-porous material and a flexible outer bag formed from a non-porous material;

providing an exothermic chemical in said flexible outer bag and a solvent in said flexible inner bag;

providing an outer flexible container having opposite ends, a first side formed of a material non-pervious to water and a second side formed from a material pervious to water, where the two sides together substantially encapsulate the flexible inner bag and the flexible outer bag;

providing a flexible sheet of heat insulating material extending over the first side of said container;

providing a water absorbent sheet made from a sponge-like material between the outer bag and the second side of the container;

contacting the second side of the container and the absorbent sheet with water so that the absorbent sheet will absorb water;

squeezing the flexible container to cause the inner bag to break and allow the exothermic chemical to mix with the solvent so as to produce heat that is directed toward the absorbent sheet to produce moist heat; and applying the flexible container, with the second side placed against said area of the body so that the moist heat will contact the skin in said area of the body.

2. The method of claim 1, including the steps of:

providing a strap extending from each of said opposite ends of said outer container; and tying said moist heating pad to said the body using said straps.

3. The method of dilating the capillary tubes in a heel of an infant child in preparation for extracting a blood sample therefrom comprising the steps of:

providing a moist heating pad dimensioned to fit over the heel of the infant having a flexible outer bag formed from a non-porous material and a flexible inner bag formed from a non-porous material;

providing an exothermic chemical in said flexible outer bag and a solvent in said flexible inner bag;

providing an outer flexible container sized to extend over the heel of the infant and engage an ankle of the infant having opposite ends, a first side formed of a material non-pervious to water and a second side formed from a material pervious to water, where the two sides together substantially encapsulate the flexible inner bag and the flexible outer bag;

providing a flexible sheet of heat insulating material extending over the first side of said container;

providing a water absorbent sheet made from a sponge-like material over the second side of the container;

contacting the second side of the container and the absorbent sheet with water so that the absorbent sheet will absorb water;

squeezing the flexible container to cause the inner bag to break and allow the exothermic chemical to mix with the solvent so as to produce heat that is directed toward the absorbent sheet to produce moist heat;

applying the flexible container, with the second side surface placed against the heel of the infant so that the moist heat will contact the skin of the heel of the infant;

and securing the moist heating pad to the ankle of the infant.

4. The method of claim 3, including the steps of:

providing a pair of straps, one each extending from each of said opposite ends of said outer container; and tying said moist heating pad to said the body using said straps.

* * * * *